United States Patent
Hilliard, Jr. et al.

(10) Patent No.: US 10,864,147 B2
(45) Date of Patent: Dec. 15, 2020

(54) ALUMINUM-FREE ANTIPERSPIRANT/DEODORANT COMPOSITIONS

(71) Applicant: Colgate-Palmolive Company, New York, NY (US)

(72) Inventors: Peter Hilliard, Jr., Far Hills, NJ (US); Sharon Kennedy, Randallstown, MD (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/469,470

(22) PCT Filed: Dec. 8, 2017

(86) PCT No.: PCT/US2017/065226
§ 371 (c)(1),
(2) Date: Jun. 13, 2019

(87) PCT Pub. No.: WO2018/111706
PCT Pub. Date: Jun. 21, 2018

(65) Prior Publication Data
US 2019/0321275 A1 Oct. 24, 2019

Related U.S. Application Data

(60) Provisional application No. 62/434,226, filed on Dec. 14, 2016.

(51) Int. Cl.
| | | |
|---|---|---|
| *A61K 8/06* | (2006.01) | |
| *A61K 8/27* | (2006.01) | |
| *A61K 8/19* | (2006.01) | |
| *A61K 8/34* | (2006.01) | |
| *A61K 8/39* | (2006.01) | |
| *A61K 8/44* | (2006.01) | |
| *A61K 8/86* | (2006.01) | |
| *A61K 8/92* | (2006.01) | |
| *A61Q 15/00* | (2006.01) | |

(52) U.S. Cl.
CPC ............... *A61K 8/27* (2013.01); *A61K 8/062* (2013.01); *A61K 8/19* (2013.01); *A61K 8/345* (2013.01); *A61K 8/347* (2013.01); *A61K 8/39* (2013.01); *A61K 8/44* (2013.01); *A61K 8/86* (2013.01); *A61K 8/922* (2013.01); *A61Q 15/00* (2013.01)

(58) Field of Classification Search
CPC ... A61K 8/06; A61K 8/19; A61K 8/27; A61K 8/34; A61K 8/39; A61K 8/44; A61K 8/86; A61K 8/92; A61Q 15/00
See application file for complete search history.

(56) References Cited

U.S. PATENT DOCUMENTS

| | | | |
|---|---|---|---|
| 5,911,975 | A | 6/1999 | Mendolia |
| 6,558,710 | B1 | 5/2003 | Godfrey |
| 7,976,828 | B2 | 7/2011 | Popoff et al. |
| 8,858,922 | B2 | 10/2014 | Grune |
| 9,707,171 | B2 | 7/2017 | Fan et al. |
| 9,750,670 | B2 | 9/2017 | Pan et al. |
| 9,757,316 | B2 | 9/2017 | Pan et al. |
| 9,827,177 | B2 | 11/2017 | Yuan et al. |
| 2003/0206973 | A1 | 11/2003 | Gale |
| 2015/0118173 | A1 | 4/2015 | Farwick et al. |

FOREIGN PATENT DOCUMENTS

| | | |
|---|---|---|
| CA | 1068215 | 12/1979 |
| JP | 5496564 | 5/2014 |
| RU | 2179015 | 5/2000 |
| WO | 2014/092688 | 6/2014 |

OTHER PUBLICATIONS

International Search Report and Written Opinion of the International Searching Authority in International Application No. PCT/US2017/065226, dated Mar. 29, 2018.

*Primary Examiner* — Zohreh A Fay

(57) ABSTRACT

An aluminum-free antiperspirant/deodorant composition is disclosed. The aluminum-free antiperspirant/deodorant composition may include an oil-in-water emulsion base and an antiperspirant active dispersed in the oil-in-water emulsion base. The antiperspirant active may be primarily an amino acid, calcium carbonate and optionally a zinc-based antiperspirant active and the oil-in-water emulsion base may include an emulsifier having a mixture of steareth-2 and steareth-20; a plant-based oil, a polyol, and water. The zinc-based antiperspirant active may be free of zinc oxide-amino acid-halide complexes, amino acid-halides, and chelated zinc oxide complexes.

16 Claims, No Drawings

ALUMINUM-FREE ANTIPERSPIRANT/DEODORANT COMPOSITIONS

BACKGROUND

Current roll-on antiperspirant/deodorant products in the market are usually emulsions, which employ the suspension of an antiperspirant active in the formulation. Various metallic salts, for example, of zinc, iron and aluminum, have been used as antiperspirant actives, with chlorohydrates and chlorides of aluminum, and aluminum and zirconium being the most commonly used antiperspirant active. However, there is a growing desire to replace these salts with other active metal salts. Zinc, which has antibacterial property, has been explored as a possible candidate to replace aluminum. However, Phinney in U.S. Pat. No. 5,512,274 reported that zinc salts precipitate as hydroxides in the range of pH of 6.5 to 8.0, and have been shown to behave erratically, being effective as an antiperspirant only for very irregular periods of time, which makes them undependable. The sporadic efficacy of zinc salts was speculated to be due to various factors, such as lack of hydrolysis conversion to relatively inactive carbonate or oxide, or some other factor or combination of factors.

Yuan and Pan, in U.S. patent publication no. 2015/0313821, reported that zinc oxide is weakly soluble at low pH. However, due to human perspiration having a pH of 5-6, the perspiration can reduce the levels of precipitation of the zinc oxide compared to precipitation levels at neutral pH. Moreover, the perspiration can gradually dissolve the depositions, reducing the duration of action of the formulation.

Hence, there remains a desire for a deodorant and/or antiperspirant/deodorant composition with increased substantivity of zinc on a skin surface.

BRIEF SUMMARY

Disclosed herein is an antiperspirant/deodorant composition comprising an oil-in-water emulsion base and an antiperspirant active dispersed in an aqueous phase of the oil-in-water emulsion base. The oil-in-water emulsion base may comprise an emulsifier comprising a mixture of steareth-2 and steareth-20, a plant-based oil, a polyol, and water. The antiperspirant active may include or consist essentially of an amino acid, calcium carbonate, and optionally a zinc-based antiperspirant active. The zinc-based antiperspirant active may be free of a zinc oxide-amino acid-halide complex, an amino acid-halide, and a chelated zinc oxide complex.

In an embodiment of the antiperspirant/deodorant composition, the zinc-based antiperspirant active comprises one or more of zinc oxide, zinc hydroxide, zinc hydroxide ions with counter ions, and zinc ions with counter ions.

In an embodiment of the antiperspirant/deodorant composition, the amino acid comprises at least one of arginine, taurine, glycine, or lysine, present in an amount of from 0.1 to 5 weight %, based on the total amount of the antiperspirant/deodorant composition.

In one embodiment of the antiperspirant/deodorant composition, the amino acid comprises calcium carbonate present in an amount of from 0.3 to 8 weight %, based on the total amount of the antiperspirant/deodorant composition.

In one embodiment of the antiperspirant/deodorant composition, the zinc-based antiperspirant active may be present in an amount of from 0.5 to 10 weight %, based on the total amount of the antiperspirant/deodorant composition.

In another embodiment of the antiperspirant/deodorant composition, the emulsifier may be present in an amount of from 0.1 to 5 weight %, based on the total amount of the antiperspirant/deodorant composition.

In yet another embodiment of the antiperspirant/deodorant composition, the emulsifier further comprises one or more of steareth-2, steareth-4, ceteareth-2, ceteareth-3, ceteareth-4, ceteareth-18, ceteareth-20, and ceteareth-22.

In one embodiment of the antiperspirant/deodorant composition, the emulsifier consists essentially of a mixture of steareth-2 and steareth-20, and wherein steareth-2 and steareth-20 are present in a weight ratio of 2.2:1 to 2.5:1.

In another embodiment of the antiperspirant/deodorant composition, the antiperspirant/deodorant composition further comprises a non-silicone based emollient present in an amount of from 0.1 to 6 weight %, based on the total amount of the antiperspirant/deodorant composition.

In yet another embodiment of the antiperspirant/deodorant composition, the non-silicone based emollient comprises one or more of isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12}$-$C_{15}$ alkyl benzoate, myreth-3 myristate, dioctyl malate, neopentyl glycol diheptanoate, dipropylene glycol dibenzoate, $C_{12}$-$C_{15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12}$-$C_{15}$ alkyl fumarate, laureth-2 benzoate propylene glycol isoceteth-3 acetate, propylene glycol ceteth-3 acetate, octyldodecyl myristate, and cetyl recinoleate, myristyl myristate, lanolate, paraffin waxes, glycyrrhizic acid, and hydrocyethyl stearate amide.

In one embodiment of the antiperspirant/deodorant composition, the non-silicone based emollient comprises diisopropyl adipate, neopentyl glycol diethylene hexanoate, and mixtures thereof.

In an embodiment of the antiperspirant/deodorant composition, the plant-based oil comprises one or more of sunflower oil, soybean oil, corn oil, jojoba oil, and methyl and/or ethyl ester derivatives thereof.

In another embodiment of the antiperspirant/deodorant composition, the plant-based oil comprises a partially hydrogenated soybean oil in an amount of 5% or less by weight.

In an embodiment of the antiperspirant/deodorant composition, the oil-in-water emulsion base further comprises at least one of a mineral oil and a synthetic oil.

In yet another embodiment, the antiperspirant/deodorant composition further comprises a film-forming polymer composition comprising at least one of a mixture of polyester-10 and propylene glycol dibenzoate; a mixture of polyester-7 and neopentyl glycol diheptanoate; adipic acid/diglycol crosspolymer; trimethylpentanediol/adipic acid/glycerin crosspolymer; trimethylpentanediol/adipic acid copolymer; capryloyl glycerin/sebacic acid copolymer; and PVM/MA decadiene crosspolymer.

In an aspect, there may be a method of reducing apparent perspiration comprising applying the antiperspirant/deodorant composition as disclosed hereinabove to an axillary area of a person, wherein the antiperspirant/deodorant composition of claim 1 reduces apparent perspiration.

In another aspect, there may be a use of the antiperspirant/deodorant composition as disclosed hereinabove to reduce perspiration on a skin surface, when tested using a method as disclosed herein, in comparison to an untreated skin surface.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

DETAILED DESCRIPTION

The following description of various preferred aspect(s) is merely exemplary in nature and is in no way intended to limit the invention, its application, or uses.

As used throughout, ranges are used as shorthand for describing each and every value that is within the range as well as the endpoints. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, the term "antiperspirant/deodorant compositions" refers to compositions which exhibit at least one of an antiperspirant effect or both an antiperspirant effect and a deodorant effect.

As used herein, the terms "zinc substantivity" and "substantivity of zinc" are used interchangeably and refer to adsorption and retention of zinc, for example in the form of zinc oxide, zinc hydroxide, zinc hydroxide ions, and/or zinc ions, on or within the top layers of a surface, such as a skin surface, and once there, resistance to subsequent removal or rinsing off of the zinc during rinsing procedure performed five times with 100 μl of 0.1 M NaCl solution to simulate perspiration or sweating.

As used herein, the term "zinc substantivity enhancer" refers to a film-forming polymer that when used in a composition containing zinc (e.g., zinc oxide) increases the substantivity of zinc on a skin surface as compared to a comparative composition without the film-forming polymer.
Compositions The antiperspirant/deodorant compositions of the present disclosure can be a liquid, a cream, or a gel. In the liquid form, the composition can be formulated to be a roll-on antiperspirant/deodorant. In one embodiment, the composition may be an oil-in-water liquid emulsion. In some embodiments or aspects, the liquid composition can be contained in any roll-on dispenser that has a ball or the like or a domed surface, for applying the antiperspirant/deodorant composition to the surface of the skin. In some other aspects, the liquid composition can be contained in an aerosol or pump spray dispenser, or a cream/gel dispenser.

In an aspect, there may be an antiperspirant/deodorant composition that may include an oil-in-water emulsion base and an antiperspirant active dispersed in an aqueous phase of the oil-in-water emulsion base, the antiperspirant active may be primarily a combination of an amino acid, calcium carbonate, and with or without a zinc-based antiperspirant active. The zinc-based antiperspirant active may include one or more of zinc oxide, zinc hydroxide, zinc hydroxide ions with counter ions, and zinc ions with counter ions, such as, for example, ZnO, $Zn^{2+}$(aq), $Zn(OH)^{+}$(aq), $Zn(OH)_2$(aq), $Zn(OH)^{-}$(aq), and $Zn(OH)^{2-}$(aq). Non-limiting examples of counter ions may include, carboxylate based fatty acid salt, amino acid salt, cationic surfactants, zwitterionic surfactant, etc. In an embodiment, the zinc-based antiperspirant active of the present disclosure may be essentially free of zinc-amino acid-halide complex. e.g. zinc-lysine-chloride (ZLC), zinc-arginine-chloride (ZAC) and/or amino acid halide precursors thereof, for example arginine hydrochloride in the case of a zinc-arginine-chloride complex. In another embodiment, the antiperspirant/deodorant composition of free of protein.

In yet another embodiment, the antiperspirant/deodorant composition may be free of chelated zinc oxide complex formed by the addition of micronized zinc oxide particles having a diameter in the range of 0.1 to 0.9 microns, distilled water, and a pH-increasing buffering agent, with buffering agent being L-arginine, sodium hydroxide, and ammonium hydroxide.

In some variation of the antiperspirant/deodorant composition, the zinc-based antiperspirant active may be free of zinc oxide-amino acid-halide complex, amino acid-halide, and chelated zinc oxide complex.

In some variations of the composition, the oil-in-water emulsion base may include water and an emulsifier that may include or may be a mixture of steareth-2 and steareth-20, a non-silicone based emollient, a plant-based oil, and a polyol.

In one aspect, the antiperspirant effect of the antiperspirant/deodorant compositions of the present disclosure may be provided by a combination of an amino acid and a zinc-based antiperspirant active, which may be zinc oxide, zinc hydroxide, zinc hydroxide ions with counter ions, and zinc ions with counter ions and/or mixtures thereof, rather than by an aluminum-based antiperspirant active. Thus, the antiperspirant/deodorant compositions described in the present disclosure are essentially free of added aluminum-based antiperspirant actives. In an embodiment, the antiperspirant/deodorant compositions described in the present disclosure are essentially free of added aluminum-based antiperspirant actives and added magnesium-based actives such as, for example, magnesium salts and magnesium hydroxide. In yet another embodiment, the antiperspirant/deodorant compositions described in the present disclosure are essentially free of added aluminum-based antiperspirant actives and added calcium-based actives other than calcium carbonate, such as, for example, calcium salts and calcium hydroxide.

By the term "essentially free of added aluminum-based antiperspirant actives, magnesium-based actives, and calcium-based actives", it is meant that aluminum-based antiperspirant actives, magnesium-based actives, and calcium-based actives are not added to the antiperspirant/deodorant composition in an amount that could display some antiperspirant/deodorant effect. However, aluminum-based antiperspirant actives, magnesium-based actives, and calcium-based actives may be present in small or trace amounts due to contamination from other ingredients used in the making of the antiperspirant/deodorant formulations of the present disclosure.

In various embodiments of the antiperspirant &/or deodorant compositions described herein, "essentially free of aluminum-based antiperspirant actives, magnesium-based actives, and calcium-based actives" means that the antiperspirant &/or deodorant compositions of the present disclosure contains less than 0.05 weight %, or less than 0.01 weight % of one or more of aluminum-based antiperspirant actives, magnesium-based actives, and calcium-based actives.

As used herein, the term "aluminum-free" means that the composition does not contain any aluminum-based antiperspirant. Non limiting examples of aluminum-based antiperspirant actives, may include those listed in US antiperspirant monograph, such as, for example, aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. In an embodiment, the antiperspirant/deodorant composition as disclosed herein may be an aluminum-free antiperspirant/deodorant composition.

Examples of magnesium-based actives may include, but are not limited to, magnesium chloride, magnesium bromide, magnesium fluoride and organic salts such as various alkyl chain length substituted carboxylic acids, magnesium oxide, and magnesium hydroxide.

The zinc-based antiperspirant active may be present in an amount of from 0.05 to 15 weight %, or 0.1 to 10 weight %, or 0.5 to 10 weight %, based on the total weight of the antiperspirant/deodorant composition. The zinc-based antiperspirant active in the form of zinc oxide can be incorporated into the antiperspirant/deodorant compositions by dispersing zinc oxide in the aqueous phase of the oil-in-water emulsion base. Zinc oxide present in the antiperspirant/deodorant composition may convert partially to zinc hydroxide or maybe present as zinc ions, or zinc hydroxide ions depending upon the pH of the final antiperspirant/deodorant composition. Hence, the amount of zinc oxide initially added to form the antiperspirant/deodorant compositions of the present disclosure may differ from the final amount of zinc oxide present in the composition due to conversion to zinc hydroxide and/or zinc ions depending upon the pH of the final antiperspirant/deodorant composition.

Any suitable amino acid may be used in combination with the zinc-based antiperspirant active for use as an antiperspirant active in the antiperspirant/deodorant composition of the present disclosure. In an embodiment, the amino acid may include at least one of arginine, taurine, glycine, or lysine. In another embodiment, the antiperspirant active may be arginine and calcium carbonate or a transition metal carbonate. In yet another embodiment, the antiperspirant active may be arginine, calcium carbonate or a transition metal carbonate and a zinc-based antiperspirant active. The amino acid may be present in an amount of from 0.1 to 4 weight %, based on the total weight of the antiperspirant/deodorant composition.

The antiperspirant/deodorant composition of the present disclosure may include calcium carbonate or a transition metal carbonate present in an amount of 0.3 to 8 weight %, based on the total weight of the antiperspirant/deodorant composition.

In an embodiment, the ratio of calcium carbonate to amino acid present in the antiperspirant/deodorant composition may be greater than 1, or greater than 1.5, or greater than 2.

Without wishing to be bound by theory, it is believed that the antiperspirant effect due to the formation of various complexes between amino acid, calcium carbonate and zinc oxide in the presence of a weak acid such as citric acid.

The pH of the antiperspirant/deodorant composition can be in the range of 3 to less than or equal to 10, or 3 to 9.8, or 3 to 9.5, or 3 to 9, or 4 to 8, or 5 to 8, or the pH can be 9, or 8, or 7, or 6.5, or 6.

Zinc Substantivity Enhancer

The antiperspirant/deodorant compositions of the present disclosure can also include a film-forming polymer to further enhance zinc sub stantivity on a skin surface. Any suitable film-forming polymer may be used in the antiperspirant/deodorant composition of the present disclosure, including but not limited to, one or more of a mixture of polyester-10 and propylene glycol dibenzoate; a mixture of polyester-7 and neopentyl glycol diheptanoate; adipic acid/diglycol crosspolymer; trimethylpentanediol/adipic acid/glycerin crosspolymer (a copolymer of trimethylpentanediol and adipic acid crosslinked with glycerin); trimethylpentanediol/adipic acid copolymer; capryloyl glycerin/sebacic acid copolymer, and PVM/MA decadiene crosspolymer (a copolymer of maleic anhydride and methyl vinyl ether crosslinked with 1,9-decadiene). Without wishing to be bound by theory, it is believed that the polyester-10 present in the hydrophobic film-forming polymer composition will spread quickly on a skin surface with improved skin feel and limited interaction with the skin. In addition, the highly water-resistant characteristics of the polyester-10 should aid in both increasing substantivity of zinc on a skin surface and also in reducing apparent perspiration by preventing sweat from reaching the skin surface.

In an embodiment, the film-forming polymer composition may be a mixture of polyester-10 and propylene glycol dibenzoate. The mixture of polyester-10 and propylene glycol dibenzoate as a film-forming polymer composition, for use as a zinc substantivity enhancer can be included in any desired amount. In one embodiment, the total amount of the film-forming polymer mixture of polyester-10 and propylene glycol dibenzoate may be in the range of 0.1 to 4.5 weight %, or 0.5 to 4 weight %, or 1.0 to 3.6 weight %, based on the total weight of the antiperspirant/deodorant composition.

The film-forming PVM/MA decadiene crosspolymer, for use as a zinc substantivity enhancer can be included in any desired amount. In one embodiment, the total amount of the film-forming polymer may be in the range of 0.1 to 5 weight %, or 0.2 to 4 weight %, or 0.25 to 3 weight %, based on the total weight of the antiperspirant/deodorant composition. Without wishing to be bound by theory, it is believed that the PVM/MA decadiene crosspolymer will interact with the Zinc in the formulation to create a hydrophobic film on the skin that enhances the water-resistant characteristics of the PVM/MA decadiene crosspolymer and increases the substantivity of zinc on a skin surface and also in reducing apparent perspiration by preventing sweat from reaching the skin surface.

Suitable examples of commercially available film-forming polymer composition may include, but are not limited to a mixture of polyester-10 and propylene glycol dibenzoate available as LexFilm® Spray; a mixture of polyester-7 and neopentyl glycol diheptanoate as LexFilm® Sun; adipic acid/diglycol crosspolymer as Lexorez® 100; trimethylpentanediol/adipic acid/glycerin crosspolymer as Lexorez® 200; trimethylpentanediol/adipic acid copolymer as Lexorez® TL-8; trimethylpentanediol/adipic acid/Glycerin crosspolymer as WetFilm™; capryloyl glycerin/sebacic acid copolymer as Vellaplex™ all from the Inolex Chemical Company of Philadelphia, Pa. Another suitable example of commercially available film-forming polymer composition may include, PVM/MA decadiene crosspolymer available as APShield™ 100, from the Ashland Specialty Ingredients Company of Bridgewater, N.J.

Oil-in-Water Emulsion Base

The antiperspirant/deodorant compositions of the present disclosure may include an oil-in-water emulsion base. The oil-in-water emulsion base may include an emulsifier that may include a mixture of steareth-2 and steareth-20, a non-silicone based emollient, a plant-based oil, a polyol, and water.

Emulsifiers

The oil-in-water emulsion base of the antiperspirant/deodorant composition of the present disclosure may include a mixture of steareth-2 and steareth-20. Steareth-2 and Steareth-20 are polyoxyethylene stearyl ethers having chemical formula: $CH_3-(CH_2)_{16}-CH_2-(O-CH_2-CH_2)_n-OH$ with average n being 2 or 20 respectively. Other stearyl ethers could be used, such as, for example, PPG-15 Stearyl Ether, which may be a polypropylene glycol ether of stearyl alcohol. However, any other suitable emulsifier can also be present in the oil-in-water emulsion base of the antiperspirant/deodorant composition. The emulsifiers can be included in any desired amount. In one embodiment, the total amount of emulsifier including Steareth-2 and Stearath-20, may be in the range of 0.5 to 12 weight %, or 0.5 to 10 weight %, based on the total weight of the composition.

Suitable emulsifiers may include, but are not limited to, Steareth-2, Steareth-4, Steareth-20, Steareth-21, Ceteareth-2, Ceteareth-3, Ceteareth-4, Ceteareth-18, Ceteareth-20, Ceteareth-22. In an embodiment, the oil-in-water base composition may include a combination of two surfactants, one having an HLB (hydrophilic-lipophilic balance) value of 2 to 8 (such as Steareth-2) and the other having an HLB of 9 to 18 (such as Steareth-20 or Steareth-21). In one embodiment, the emulsifier present in the antiperspirant/deodorant composition of the present disclosure may be primarily or essentially a mixture of steareth-2 and steareth-20. In such embodiments, the steareth-2 and steareth-20 are present in a weight ratio of 2.2:1 to 2.5:1, or 1:1 to 1.75:1, or 1:1 to 1.2:1.

Steareth-2 and Steareth-20 are polyoxyethylene stearyl ethers having chemical formula: $CH_3-(CH_2)_{16}-CH_2-(O-CH_2-CH_2)_n-OH$ with average n being 2 or 20 respectively. It has been a surprising discovery that steareth-2 has been found to have a positive effect on increasing the zinc substantivity and comparison steareth-20 has been found to have a negative effect on the zinc substantivity. Without wishing to be bound by theory, it is believed that it is the difference in the balance of hydrophilic and lipophilic parts of Steareth-2 and Steareth-20 that results in opposite effect. Steareth-2 with short ethylene oxide chain may be a water-in-oil emulsifier, as the hydrophilic part may be smaller than and subordinate to the lipophilic part. The relatively longer lipophilic part of Steareth-2 is believed to help in an increase in zinc substantivity.

Non-Silicone Based Emollient

The antiperspirant/deodorant composition can contain any suitable non-silicone based emollient in any desired amount to achieve a desired emollient effect. In one embodiment, the amount of emollients may be less than 15%, or less than 11%, or in the range of 0.1 to 8 weight % or 0.1 to 6 weight %, based on the total weight of the composition. Emollients are known in the art and are used to impart a soothing effect on the skin.

Suitable non-silicone based emollients may be selected from among isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12}$-$C_{15}$ alkyl benzoate, myreth-3 myristate, dioctyl malate, neopentyl glycol diheptanoate, dipropylene glycol dibenzoate, $C_{12}$-$C_{15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12}$-$C_{15}$ alkyl fumarate, laureth-2 benzoate propylene glycol isoceteth-3 acetate, propylene glycol ceteth-3 acetate, octyldodecyl myristate, and cetyl recinoleate, myristyl myristate, isopropyl, lanolate, paraffin waxes, glycyrrhizic acid, and hydrocyethyl stearate amide.

In an embodiment, the non-silicone based emollient includes one or more of diisopropyl adipate and neopentyl glycol diethylene xanoate.

Polyols

The polyol may be selected from among ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, 1,2-octanediol (capryl glycol), PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof. More particular examples of the glycol component may include one or more of propylene glycol, dipropylene glycol, tripropylene glycol, 2-methyl-1,3-propanediol, methyl propylene glycol, low molecular weight (less than 600) polyethylene glycol, low molecular weight (less than 600) polypropylene glycols, and mixtures of any of the foregoing. Mixtures of glycols may be used. In an embodiment, the oil-in-water emulsion base of the present antiperspirant/deodorant composition includes 1,2-octanediol (capryl glycol). The polyol maybe present in any suitable amount, such as in the range of 0.2 to 0.3 weight %, or 0.2 to 0.4 weight %, or 0.2 to 0.6 weight %, or 0.2 to 0.9 weight %, based on the total weight of the composition.

Plant-Based Oils

In various embodiments, the antiperspirant &/or deodorant compositions disclosed herein may include a plant-based oil having a melting point of −15 to 38° C., which may be an oil that may be obtained from a plant or may be a synthetically manufactured equivalent. These can include common triglycerides such as sunflower oil, soybean oil, corn oil as non-limiting examples. As used herein, the term oil may include materials that are defined as a liquid wax. For example, jojoba oil can be referred to as a liquid wax. The methyl and ethyl esters of plant-derived oils may also be included in the definition of a plant-derived oil. This plant-derived oil can provide structure to the composition, and thus, yield to suspend materials with densities significantly different from the emulsion base. In one embodiment, this material may be present in an amount of 5% or less by weight of the composition. Levels much higher than 5% may give an oily/greasy feel to the composition and cause an undesirable increase in drying time on the skin. In one embodiment, the amount of plant-derived oil may be 1 to 5% by weight of the composition. Examples of the plant-derived oil may include, but are not limited to, soybean oil, jojoba oil, coconut oil, safflower oil, palm kernel oil, cottonseed oil, and pine nut oil. In certain embodiments, the plant-derived oils are partially hydrogenated versions of these oils. Lower levels of unsaturation, such as high oleic sunflower oil verses normal sunflower oil, can reduce potential chemical interaction with other roll-on components and can also reduce the tendency for the oil to oxidize and form a rancid odor that may be harder to fragrance. The iodine value and percent saturates (which are inversely proportional to each other) are two means of describing the degree of hydrogenation present in the plant-derived oil.

One of the advantages of the presence of the plant-derived oil in the antiperspirant/deodorant composition is that the plant-derived oils reduces the tackiness of the antiperspirant active, which is found in the aqueous phase. The addition of non-silicon based emollients in combination with the plant-derived oil can also give this desired effect when the total amount of emollient and the plant-derived oil is less than 7 weight %, or less than 3.7 weight %, or less than 3.5 weight %, based on the total weight of the antiperspirant/deodorant composition. In various tests, the tackiness was determined by an expert sensory panel included of at least 10 trained panelists who assess the skin feel properties of the formulas. One of the product characteristics measured in the tests, both on forearm and axillary, was tackiness. The trained panelists assessed the tackiness of the product formulas by feeling the product with their fingertips at given time intervals and rating the tackiness on a scale of 0 (no tack) to 10 (very tacky).

Ameliorating the wet feeling can also be achieved by providing some structure and body to the formula that the wearer perceives as providing a richness to the formula.

In one embodiment, the plant-derived oil may be selected to be partially hydrogenated and have a melting point that may be −15° C. (5° F.) to 38° C. (100° F.). In another embodiment, the melting point may be 26° C. (80° F.) to 35° C. (95° F.). To obtain the desired melting point, the plant-derived oil can be partially hydrogenated or a blend of non-hydrogenated with partially or fully hydrogenated oils and/or waxes can be used.

In an embodiment of the antiperspirant/deodorant composition, the plant-based oil may be a partially hydrogenated soybean oil in an amount of 5% or less by weight, based on the total weight of the composition. In another embodiment of the antiperspirant/deodorant composition, the plant-based oil includes a partially hydrogenated soybean oil with a melting point of 26 to 38° C.

In one embodiment, the plant-based oil may be a partially hydrogenated soybean oil having an iodine value in the range of 75 to 80. Iodine value can be measured according to ASTM D5554-95 (2006). This partially hydrogenated soybean oil can be obtained from Cargill under the product designation S-500.

Another benefit of using a partially hydrogenated plant oil such as soybean oil in an emulsion is that it can provide structure, in the form of increased viscosity, to the antiperspirant/deodorant composition. Viscosity or structure of a liquid antiperspirant/deodorant composition was measured in mPas (centipoise) by a Brookfield Viscometer at 23° C. using spindle 4 at an RPM setting of 20. In an embodiment, the antiperspirant/deodorant composition has a viscosity in the range of 600 to 4500 mPa, or 700 to 4000 mPa, or 900 to 3000 mPa or 1500 to 3000 mPa, measured at 23° C. In another embodiment, the antiperspirant/deodorant composition, as disclosed herein above, that further may include a film forming polymer as a zinc substantivity enhancer, can have a viscosity in the range of 500-30,000 mPa.

An additional benefit of using a partially hydrogenated plant oil such as soybean oil within the present disclosure is that it increases the ease of fragrancing the antiperspirant/deodorant compositions. The reduced level of malodor formed during the aging of the composition when formulating with partially hydrogenated plant oils allows the fragrance to act only or mostly for pleasant hedonic purposes without having to also cover a malodor. Partially hydrogenated plant oils have a lower iodine value, which corresponds to fewer double bonds. The reduced number of double bonds provides a lower propensity for fragrance degradation, i.e., malodor.

In an embodiment of the antiperspirant/deodorant composition, the oil-in-water emulsion base may further include mineral oil and/or synthetic oil. Any suitable mineral oil that is colorless, odorless, a mixture of higher alkanes from a mineral source, particularly a distillate of petroleum can be used. Suitable synthetic oils may include, but are not limited to Group IV base oils and Group V base oils. A Group IV base oil is a poly-alpha-olefin (or poly-α-olefin, abbreviated as PAO), a polymer made by polymerizing an alpha-olefin. Group V base oils are defined by API as any other type of oil other than mineral oils or PAO lubricants. Synthetics Esters are the most famous synthetics in Group V, which may be 100% synthetic chemical compounds consisting of a carbonyl adjacent to an ether linkage. They may be derived by reacting an oxoacid with a hydroxyl compound such as an alcohol or phenol. Esters may usually be derived from an inorganic acid or organic acid in which at least one —OH (hydroxyl) group may be replaced by an —O-alkyl (alkoxy) group, most commonly from carboxylic acids and alcohols. That is to say, esters may be formed by condensing an acid with an alcohol, or Semi-synthetic blends of synthetic oils and mineral oils.

Water

The antiperspirant/deodorant composition of the present disclosure may also include water to form the oil-in-water emulsion base. Water may be present in an any suitable amount capable of producing a stable emulsion to make a 100% by weight composition after all of the materials, including any optional materials, may be added to the composition in their desired weight percentages. In certain embodiments, the amount of water may be at least 20%, 30%, 40%, 50%, 60%, 70%, 80%, or 85% by weight of the composition.

The total solids of the composition is, for example, the amount of non-volatile materials in the composition. The total solids of the composition can be measured by a CEM Smart System moisture/solids analyzer which uses microwave energy to dry the samples. In one embodiment, the total solids may be less than 25 weight %, based on the total weight of the original, undried composition. In another embodiment, the amount of total solids may be less than 20 weight %, based on the total weight of the undried composition.

Optional Ingredients

The antiperspirant/deodorant compositions of the present disclosure may also include other ingredients. For example, the antiperspirant/deodorant compositions of the present disclosure may include one or more ingredients for achieving and maintaining a desired consistency, one or more ingredients for giving the product a soothing skin feel, one or more antioxidants, one or more fragrances and one or more ingredients for fragrance duration or retention, and additional deodorizing agent. Some ingredients listed herein can provide more than one function to the compositions. For example, certain emollients can act as lipophilic carrier material and a gelling agent at the same time.

Non-limiting examples of ingredients suitable for use as skin soothing agents may be, for example, aloe vera leaf extract or juice, chamomile aqueous extract, other herbal extracts and oatmeal. Non-limiting examples of astringents may include, for example witch hazel water. The present antiperspirant/deodorant compositions may include one or more of aloe vera leaf extract or juice present in an amount of 0.5 to 10 weight %, witch hazel (also known as witch hazel water) present in an amount of 1 to 10 weight %, and chamomile aqueous extract present in an amount of 1 to 20 weight %, based on the total weight of the antiperspirant/deodorant composition.

Non-limiting examples of ingredients suitable for use as antioxidants may be, for example, one or more of tocopherol and its derivatives, butyl hydroxyanisole (BHA), butyl hydroxytoluene (BHT), erythorbic acid, propyl gallate, sodium erythorbate, tertiary butyl hydroquinone (TBHQ), rosemary extract and, more preferably, ascorbic acid and salts thereof. The antioxidant compound may be one or more of tocopherol and its derivatives present in an amount of 0.001 to 0.5 weight %, or butyl hydroxyanisole (BHA) present in an amount of 0.0075 to 0.1 weight %, butyl hydroxytoluene (BHT) present in an amount of 0.005 to 0.02 weight %, erythorbic acid present in an amount of 0.05 to 1 weight %, propyl gallate present in an amount of 0.01 to 1 weight %, sodium erythorbate present in an amount of 0.05 to 1 weight %, tertiary butyl hydroquinone (TBHQ) present in an amount of 0.005 to 0.1 weight %, rosemary extract present in an amount of 0.02 to 0.4 weight %, and ascorbic acid and salts thereof present in an amount of 0.01 to 0.1 weight %, based on the total weight of the antiperspirant/deodorant composition.

The antiperspirant/deodorant compositions of the present disclosure may include natural and synthetic fragrance(s), if a scented product is desired. Fragrances can be used in any suitable amount, such as in the range of 0.01 to 3%, and, for example, at a level of about 1%.

The antiperspirant/deodorant compositions of the present disclosure may also include ingredients suitable for use for fragrance duration or longevity, such as, for example silica shells, polymeric, or other encapsulates compatible with antiperspirant/deodorant base formulation.

The antiperspirant/deodorant compositions of the present disclosure may include additional deodorizing compounds, antimicrobials, and/or preservatives, for example, including but not limited to, capryl glycol, glyceryl laurate, capric triglyceride, benzoic acid, sodium benzoate, hydroxybenzoate and derivatives, lactic acid, phenoxyethanol, ethoxy hexyl glycerine, benzyl alcohol, Kathon™ and Kathon™ CG, present in an amount of 0.1 to 4 weight %, and lemongrass oil present in an amount of 0.01 to 0.1 weight %, based on the total weight of the antiperspirant/deodorant composition.

Additional gelling agent(s) such as, fatty alcohols may be incorporated into the antiperspirant/deodorant compositions of the present disclosure. In one embodiment, the fatty alcohol may be stearyl alcohol or docosyl alcohol (behenyl alcohol).

Various embodiments of the antiperspirant/deodorant compositions of the present disclosure may be suitable for use as roll-on compositions to be stored/dispensed in roll-on type containers or other types of containers from which a viscous liquid can be dispensed, as are known in the art. The components of conventional roll-on containers can be made of various materials and can have different shapes, as is known in the art. For example, the material of the container can be polypropylene, polyethylene terephthalate (PET), high-density polyethylene or glass. The applicator may be usually a hollow ball made of polypropylene. The ball's diameter can vary from 10 to 36 mm, depending on the design of the container. The ball can be assembled directly in the container or with a special insert (ball housing) depending also on the design of the container. The caps can be of different designs (usually made of polypropylene) with smooth or ribbed walls.

Examples of suitable roll-on dispensers may include those described in U.S. Des. Pat. No. 402,550 to Poisson; U.S. Pat. No. 6,132,126 to Sheffer et al (an adjustable applicator); U.S. Pat. No. 4,030,844 to Lench et al; U.S. Pat. No. 4,021,125 to Berghahn et al; U.S. Pat. No. 4,033,700 to Spatz; U.S. Pat. No. 5,553,957 to Dombusch et al; WO 00/64302 to Hindustan Lever Ltd.; and PCT Patent Appl. Publ. No. WO 01/03541 to Chang; all of which are incorporated by reference herein to the extent they describe roll-on dispensers. Domed containers which mimic a roll-on dispenser without a movable ball can also be used to apply the product. Stick type containers with flat or curved heads containing holes thru which the product can be extruded upon dispensing without a movable ball can also be used to apply the product.

Zinc Substantivity

The antiperspirant/deodorant composition provides excess zinc substantivity on skin [e.g., from zinc oxide, or zinc hydroxide, zinc hydroxide ions, or zinc ions] in an amount of at least 8 picoMoles or at least 50 picoMoles per 0.34 $cm^2$ of skin surface, as measured by the method disclosed hereinbelow.

As used herein, the zinc substantivity may be measured by applying a sample of the antiperspirant/deodorant composition onto a sample of pig skin and equilibrating in a hydrated form for 15 hours at approximately 38° C., followed by rinsing the pig skin five times with 100 µl of 0.1 M NaCl solution to simulate perspiration or sweating. A color-changing zinc-sensitive dye solution was then applied to the pig skin and the amount of zinc was determined from the color change. The method of measuring zinc substantivity is described in details below under Example section.

Without wishing to be bound by theory, it is believed that the testing for zinc substantivity done on pig skin using an NaCl solution to simulate sweating on human skin is representative of zinc substantivity provided by the antiperspirant/deodorant composition of the present disclosure on human skin.

Methods/Uses

In an aspect, there may be a method of making an aluminum-free antiperspirant/deodorant composition comprising the steps of:
a) forming an aqueous phase by mixing an emulsifier comprising steareth-20 with water and polyol;
b) forming an oil phase by mixing an emulsifier comprising Steareth-2 with a plant-based oil;
c) adding the oil phase to the aqueous phase to form an oil-in-water emulsion base;
d) adding a mixture of a weak acid, an amino acid and calcium carbonate in water to the oil in water emulsion base, followed by optional addition of zinc oxide, to form an aluminum-free antiperspirant/deodorant composition, such that the pH of the antiperspirant/deodorant composition may be less than 10.

In contrast, the chelated zinc oxide complex of U.S. Pat. No. 8,858,922 is formed at a pH greater than 10, by the addition of micronized zinc oxide particles, distilled water, and a pH-increasing buffering agent, with buffering agent being L-arginine, sodium hydroxide, and ammonium hydroxide, as a premix, to be added to the base formulation.

In an embodiment of the method of making an aluminum-free antiperspirant/deodorant composition, various steps may be carried out at a temperature in the range of 60–80° C.

A non limiting example of a weak acid used in the making of the antiperspirant/deodorant composition may include citric acid.

In an aspect, there may be a method of reducing apparent perspiration including applying the antiperspirant/deodorant composition, as disclosed hereinabove to an axillary area of a person, wherein the antiperspirant/deodorant composition reduces apparent perspiration, wherein the reduction is in comparison to an antiperspirant/deodorant composition without the zinc oxide.

In another aspect, the antiperspirant &/or deodorant compositions as disclosed hereinabove can be used to increase substantivity of zinc on a skin surface, when tested using methods as disclosed hereinabove.

In yet another aspect, a zinc substantivity enhancer can be used in the antiperspirant/deodorant composition as disclosed hereinabove to increase zinc retention when applied to an axillary area, such as an armpit, wherein the substantivity enhancer may be any suitable hydrophobic film-forming polymer compatible with the oil-in-water emulsion compositions, as disclosed hereinabove. An exemplary hydrophobic film-forming polymer may include a mixture of polyester-10 and propylene glycol dibenzoate.

The antiperspirant/deodorant composition of the present disclosure when applied on a skin surface provides a reduction in sweat/perspiration in an amount of at least 6%, or at least 35%, as measured by the method disclosed hereinbelow, and in comparison to a skin surface without treatment with any antiperspirant/deodorant composition (i.e. untreated skin surface). In certain embodiments, the application may be to axilla.

The antiperspirant &/or deodorant compositions of the present disclosure provide several advantages and improvements over conventional antiperspirant &/or deodorant compositions. First and foremost is that the antiperspirant/deodorant compositions are free of added aluminum-based antiperspirant actives, as aluminum has been shown to have adverse side effects in some people. Secondly, the antiperspirant/deodorant compositions as disclosed hereinabove including a combination of arginine and zinc oxide provides greater antiperspirant benefit—greater % sweat reduction with lower amount of zinc oxide as compared to a comparative antiperspirant/deodorant composition having an identical composition as that of the antiperspirant/deodorant composition of the present disclosure, except that the comparative antiperspirant/deodorant composition has either L-arginine or zinc oxide. Without wishing to be bound by theory, it is believed that the presence of L-arginine may also provide increased zinc substantivity, which could result in a decrease in the amount of zinc oxide needed to be delivered from the antiperspirant/deodorant compositions and hence a decrease in the overall amount of zinc oxide present in the antiperspirant/deodorant compositions, which in turn decreases the cost of manufacture of these antiperspirant/deodorant compositions. Lastly, the use of plant-based oils and non-silicone based emollients provides formula stability, glideability, increased skin softness and moisturization, low residue, and fast drying.

In yet another aspect, a zinc substantivity enhancer can be used in the antiperspirant/deodorant composition as disclosed hereinabove to increase zinc retention when applied to an axillary area, such as an armpit, wherein the substantivity enhancer may be a film-forming polymer composition including PVM/MA decadiene crosspolymer.

EXAMPLES

Antiperspirant Efficacy by Measurement of Sweat Reduction

A balanced block design was used to evaluate n different antiperspirant/deodorant compositions (product) with $n \leq 11$, and an untreated control (U) using (n+1) sites on the back of approximately 30 panelists. The n products and the untreated control were randomly assigned to the (n+1) sites following a randomization code, such that an equal number of products were assigned to each of the (n+1) possible locations. The inclusion of an untreated control allowed paired comparisons of each active product and the untreated control. Products were assigned to each site after ranking the panelists in order of highest to lowest sweat output at baseline (mean of the (n+1) sites) following the randomization code. Sweat amounts were measured gravimetrically by weighing Webril pads before and after sweating and obtaining the weight difference due to absorbed sweat.

An analysis of covariance (ANCOVA) model was used to compare percent change from baseline untreated control site. The logarithm of the sweat production was the dependent variable in the model and the independent terms included panelists, log baseline sweat output, location on the back, treatment composition (product). The model used herein for analysis was an extension of the SSEM model proposed by Levine and Murphy (Murphy TD and Levine MJ: Analysis of Antiperspirant Efficacy Test Results, J. Soc. Cosmet. Chem., 42, 167-197, May-June 1991). The use of this statistical model would be obvious to one of ordinary skilled in the art.

% Sweat Reduction was calculated using following equation:

$$\% \text{ Sweat Reduction} = 100 \times \left[ 1 - \frac{\text{Amount of sweat from treated site}}{\text{Amount of sweat from untreated control site}} \right]$$

Example 1: Preparation of Aluminum-Free Antiperspirant/Deodorant Composition Including Zinc Oxide and L-Arginine The aluminum-free antiperspirant/deodorant composition including added zinc oxide is an oil in water emulsion consisting of an aqueous phase and an oil phase. The process of making such a formulation is described below:

To make the aqueous phase: DI water was added to a beaker and heated up to 70° C. Then, steareth-20 was added and mixed until dissolved. At last, capryl glycol was added and mixed for 5 min.

To make the oil phase: PPG-15 Stearyl ether, Steareth-2, soybean oil, BHT, and optional oleic acid were added to a separate beaker and heated to 60° C. while stirring.

To create the emulsion: The oil phase was added to the aqueous phase while homogenizing at 55 rpm for 3 min with the Greeco homogenizer.

Adding Caustic and Active (in lieu of the step of adding acid and active): Added sodium hydroxide to the remaining water and upon completion of the homogenization, added the water/caustic into the beaker with the emulsion, followed by addition of zinc oxide at 30° C. with continued stirring at 200 rpm for 1.5 hours. Cooled batch after homogenizing.

Adding Acid and Active (in lieu of the step of adding caustic and active): Added citric acid, arginine and calcium carbonate to the remaining water and added this water mixture into the beaker with the emulsion, followed by addition of optional zinc oxide at 30° C. with continued stirring at 200 rpm for 1.5 hours. Cooled batch after homogenizing.

Various antiperspirant/deodorant compositions made using the method described above are summarized in the Table 1.

Also, comparing Comparative Example 2 and Example 1 shows that with the use of a combination of arginine and zinc oxide, the amount of zinc oxide can be reduced from 2 to 1 weight % and at the same time greater antiperspirant benefit—greater % sweat reduction can be achieved. Comparing Comparative Examples A and C shows that similar reduction in sweat can be achieved by either using 2 weight % zinc oxide or by using 1 weight % arginine. Comparing Comparative Examples A and B shows that 2 weight % zinc oxide with 1 weight % oleic acid provides better benefit—

| Aluminum-free Antiperspirant/deodorant composition, Amounts in weight % | | | | |
|---|---|---|---|---|
| | Comparative Example A | Comparative Example B | Example 1.1 | Example 1.2 |
| L-Arginine | 0.00 | 0.00 | 1.00 | 1.00 |
| Precipitated Calcium carbonate | 0.00 | 0.00 | 2.50 | 2.50 |
| Zinc oxide | 2.00 | 5.00 | 0.00 | 1.00 |
| Oleic acid | 1.00 | 0.00 | 0.00 | 0.00 |
| Steareth-2 | 2.20 | 2.20 | 2.50 | 2.50 |
| Steareth-20 | 2.00 | 2.00 | 2.50 | 2.50 |
| Capryl glycol | 0.60 | 0.60 | 0.60 | 0.60 |
| PPG-15 Stearyl ether | 2.45 | 2.45 | 2.50 | 2.50 |
| Hydrogenated soybean oil (S5) with BHT | 3.00 | 3.00 | 3.00 | 3.00 |
| Di-tertiray butyl-para-cresol (BHT) | 0.05 | 0.05 | 0.05 | 0.05 |
| Sodium hydroxide-50% | 0.006 | 0.006 | 0.000 | 0.000 |
| Citric acid 50% solution | 0.00 | 0.00 | 0.20 | 0.60 |
| Dimineralized water | Q.S. | Q.S. | Q.S. | Q.S. |
| pH | 7.50 | 7.03 | 8.85 | 8.86 |
| Viscosity (centiPoise) | 1760 | 1990 | 1330 | 2020 |

Antiperspirant Efficacy by Measurement of Sweat Reduction of Antiperspirant/Deodorant Compositions The antiperspirant efficacy of each of the antiperspirant/deodorant compositions shown in Table 1 was determined by measuring % sweat reduction using the procedure described hereinabove. The antiperspirant/deodorant compositions and the sweat reduction results are also summarized in Table 2.

TABLE 2

| % Sweat reduction based on sweat weight vs control untreated site. | | | |
|---|---|---|---|
| | Aluminum-free Roll On Antiperspirant/deodorant composition | % Sweat Reduction versus untreated control site | Statistical group ($p < 0.5$) |
| Comparative Example A | 2 weight % ZnO with 1% Oleic Acid | 10.2 | c, d, e |
| Comparative Example B | 5 weight % ZnO | 4 | d, e |
| Example 1.1 | 1 weight % L-Arginine and 2.5 weight % Calcium carbonate | 10.4 | c, e |
| Example 1.2 | 1 weight % ZnO, 1 weight % Arginine, and 2.5 weight % Calcium carbonate | 15.9 | b, c |

Table 2 shows that the among all the of aluminum-free compositions tested as compared to untreated sites, the composition including a combination of zinc oxide and arginine (Example 1) shows the greatest % sweat reduction.

greater reduction in sweat as compared to using only 5 weight % zinc oxide, while keeping all the other ingredients the same.

What is claimed is:

1. An aluminum-free antiperspirant/deodorant composition comprising:
    an oil-in-water emulsion base comprising:
        an emulsifier comprising a mixture of steareth-2 and steareth-20,
        a plant-based oil,
        a polyol, and
        water; and
    an antiperspirant active dispersed in the oil-in-water emulsion base, wherein the antiperspirant active consists essentially of an amino acid, calcium carbonate, and a zinc-based antiperspirant active,
    wherein the zinc-based antiperspirant active is free of zinc oxide-amino acid-halide complex, amino acid-halide, and chelated zinc oxide complex, and
    wherein complexes are formed between the amino acid, calcium carbonate and the zinc-based antiperspirant active.

2. The antiperspirant/deodorant composition of claim 1, wherein the amino acid comprises at least one of arginine, taurine, glycine, or lysine, and wherein the amino acid is present in an amount of from 0.1 weight % to 4 weight %, based on the total amount of the antiperspirant/deodorant composition.

3. The antiperspirant/deodorant composition of claim 1, wherein the calcium carbonate is present in an amount of from 0.3 weight % to 8 weight %, based on the total amount of the antiperspirant/deodorant composition.

4. The antiperspirant/deodorant composition of claim 1, wherein the zinc-based antiperspirant active comprises one or more of zinc oxide, zinc hydroxide, zinc hydroxide ions with counter ions, and zinc ions with counter ions.

5. The antiperspirant/deodorant composition of claim 1, wherein the zinc-based antiperspirant active is present in an amount of from 0.5 weight % to 10 weight %, based on the total amount of the composition.

6. The antiperspirant/deodorant composition of claim 1, wherein the emulsifier is present in an amount of from 0.5 to 5 weight %, based on the total amount of the antiperspirant/deodorant composition.

7. The antiperspirant/deodorant composition of claim 1, wherein the emulsifier further comprises one or more of steareth-2, steareth-4, ceteareth-2, ceteareth-3, ceteareth-4, ceteareth-18, ceteareth-20, and ceteareth-22.

8. The antiperspirant/deodorant composition of claim 1, wherein the emulsifier consists essentially of a mixture of steareth-2 and steareth-20, and wherein steareth-2 and steareth-20 are present in a weight ratio of 2.2:1 to 2.5:1.

9. The antiperspirant/deodorant composition of claim 1, wherein the antiperspirant/deodorant composition further comprises a non-silicone based emollient present in an amount of from 0.1 to 6 weight %, based on the total amount of the antiperspirant/deodorant composition.

10. The antiperspirant/deodorant composition of claim 9, wherein the non-silicone based emollient comprises one or more of isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, C12-C15 alkyl benzoate, myreth-3 myristate, dioctyl malate, neopentyl glycol diheptanoate, dipropylene glycol dibenzoate, C12-C15 alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, C12-C15 alkyl fumarate, laureth-2 benzoate propylene glycol isoceteth-3 acetate, propylene glycol ceteth-3 acetate, octyldodecyl myristate, and cetyl recinoleate, myristyl myristate, lanolate, paraffin waxes, glycyrrhizic acid, and hydrocyethyl stearate amide.

11. The antiperspirant/deodorant composition of claim 9, wherein the non-silicone based emollient comprises diisopropyl adipate, neopentyl glycol diethylene hexanoate, and mixtures thereof.

12. The antiperspirant/deodorant composition of claim 1, wherein the plant-based oil comprises one or more of sunflower oil, soybean oil, corn oil, jojoba oil, and methyl and/or ethyl ester derivatives thereof.

13. The antiperspirant/deodorant composition of claim 1, wherein the plant-based oil comprises a partially hydrogenated soybean oil in an amount of 5% or less by weight.

14. The antiperspirant/deodorant composition of claim 1, wherein the oil-in-water emulsion base further comprises at least one of a mineral oil and a synthetic oil.

15. The antiperspirant/deodorant composition of claim 1 further comprising a film-forming polymer composition comprising at least one of a mixture of polyester-10 and propylene glycol dibenzoate; a mixture of polyester-7 and neopentyl glycol diheptanoate; adipic acid/diglycol crosspolymer; trimethylpentanediol/adipic acid/glycerin crosspolymer; trimethylpentanediol/adipic acid copolymer; capryloyl glycerin/sebacic acid copolymer; and PVM/MA decadiene crosspolymer.

16. A method of reducing apparent perspiration comprising applying the antiperspirant/deodorant composition of claim 1 to an axillary area of a person, wherein the antiperspirant/deodorant composition of claim 1 reduces apparent perspiration.

\* \* \* \* \*